(12) United States Patent
Lee et al.

(10) Patent No.: US 7,351,238 B2
(45) Date of Patent: Apr. 1, 2008

(54) CATHETER HAVING A REINFORCING MANDREL

(75) Inventors: Jeong Soo Lee, Diamond Bar, CA (US); Tim Geiser, Temecula, CA (US); Sandra K. Schenk, San Jose, CA (US); Terry Freeman, Murrieta, CA (US); Cheri Stiger, Escondido, CA (US); Fozan El-Nounou, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 541 days.

(21) Appl. No.: 10/692,365

(22) Filed: Oct. 22, 2003

(65) Prior Publication Data

US 2004/0082935 A1    Apr. 29, 2004

Related U.S. Application Data

(62) Division of application No. 09/470,519, filed on Dec. 22, 1999, now Pat. No. 6,733,486.

(51) Int. Cl.
*A61M 25/00* (2006.01)

(52) U.S. Cl. .................................................. 604/525

(58) Field of Classification Search ........ 604/523–525, 604/96.01, 164.13, 154.12
See application file for complete search history.

(56) References Cited

U.S. PATENT DOCUMENTS

| | | | |
|---|---|---|---|
| 4,762,129 A | 8/1988 | Bonzel | |
| 4,979,951 A | 12/1990 | Simpson | |
| 5,180,367 A | 1/1993 | Kontos et al. | |
| 5,224,933 A | 7/1993 | Bromander | |
| 5,242,396 A | 9/1993 | Evard | |
| 5,387,193 A | 2/1995 | Miraki | |
| 5,425,711 A | 6/1995 | Ressemann et al. | |
| 5,507,768 A | 4/1996 | Lau et al. | |
| 5,531,690 A | 7/1996 | Solar | |
| 5,549,552 A | 8/1996 | Peters et al. | |
| 5,562,620 A * | 10/1996 | Klein et al. ............ | 604/103.01 |
| 5,607,394 A | 3/1997 | Andersen et al. | |
| 5,634,902 A * | 6/1997 | Johnson et al. .......... | 604/96.01 |
| 5,782,740 A | 7/1998 | Schneiderman | |

(Continued)

FOREIGN PATENT DOCUMENTS

EP    0 515 119 A1    11/1992

(Continued)

*Primary Examiner*—Kevin C. Sirmons
*Assistant Examiner*—Catherine N. Witczak
(74) *Attorney, Agent, or Firm*—Fulwider Patton LLP (57) ABSTRACT

A catheter having a mandrel secured to the catheter or constrained within a dedicated lumen. In one embodiment, the catheter has an inner tubular member and an outer tubular member with a sidewall configured to define a mandrel lumen longitudinally along an inner surface of the outer tubular member or along an outer surface of the inner tubular member. The mandrel lumen may be configured to allow the mandrel to be exchanged to adjust the handling characteristics of the catheter. The mandrel may occupy an intermediate portion of the catheter shaft, or may extend from the proximal end to within proximal or distal shaft sections of the catheter. In coronary artery applications, the mandrel is configured to support the catheter as it bends through the aortic arch and enters the coronary artery.

15 Claims, 4 Drawing Sheets

U.S. PATENT DOCUMENTS

| | | |
|---|---|---|
| 5,795,325 A | 8/1998 | Valley et al. |
| 5,810,867 A | 9/1998 | Zarbatany et al. |
| 5,823,995 A | 10/1998 | Fitzmaurice et al. |
| 5,868,706 A | 2/1999 | Cox |
| 5,882,336 A | 3/1999 | Janacek |
| 5,897,536 A | 4/1999 | Nap et al. |
| 5,931,812 A | 8/1999 | Andersen et al. |
| 6,733,486 B1 * | 5/2004 | Lee et al. .................. 604/525 |
| 2006/0129178 A1 * | 6/2006 | Reifart et al. ............... 606/192 |

FOREIGN PATENT DOCUMENTS

| | | |
|---|---|---|
| EP | 0832670 A1 | 1/1998 |
| EP | 0835673 A2 | 4/1998 |
| WO | WO 92/17236 | 10/1992 |
| WO | WO 96/20752 | 7/1996 |

* cited by examiner

CATHETER HAVING A REINFORCING MANDREL

This application is a divisional of application Ser. No. 09/470,519, filed Dec. 22, 1999, issued May 11, 2004 as U.S. Pat. No. 6,733,486.

BACKGROUND OF THE INVENTION

This invention relates to the field of medical devices, and more particularly to a balloon catheter having a reinforcing mandrel.

Catheters designed for intravascular procedures such as angioplasty have a number of desirable characteristics. Such catheters must be able to transmit force along the length of the catheter shaft to allow it to be pushed through the vasculature. However, the catheter shaft must also retain sufficient flexibility to allow it to track over a guidewire through the often tortuous vasculature. Additionally, the catheter also must be able to cross stenosed portions of the vascular anatomy.

To help meet the desire for a catheter having sufficient pushability and crossability, while maintaining trackability, prior art designs have supplemented polymer catheter shafts with a stiffening wire or mandrel. Other prior art designs have addressed these handling and performance issues by using materials of different stiffness for the proximal and distal portions of the catheter, and employing a high strength metallic proximal shaft section, commonly called a hypotube. To prevent kinking at the junction of these two materials, while maintaining trackability and pushability, some conventional designs have employed a stiffening wire to bridge the transition in catheter shaft material. Despite these attempts, prior art designs have suffered from various drawbacks. For example, support mandrels do not always transmit axial force effectively.

Accordingly, it would be a significant advance to provide a catheter having improved pushability and crossability while maintaining good trackability. This invention satisfies these and other needs.

SUMMARY OF THE INVENTION

The invention is directed to catheters having supporting mandrels to improve pushability and trackability. The mandrel is constrained within the catheter shaft by being located within a dedicated mandrel lumen or secured at least in part directly to the catheter shaft. The length and position of the mandrel within the catheter shaft may vary, so that the mandrel extends distally from the proximal end of the catheter shaft, or alternatively, from a location distal to the proximal end of the catheter shaft. The term mandrel should be understood to include a variety of different supporting members such as solid or hollow rods, wires, and the like.

One embodiment of the catheter of the invention comprises an inner tubular member defining a guidewire lumen and an outer tubular member coaxially or eccentrically disposed about the inner tubular member to form an annular inflation lumen, with a side wall which extends longitudinally within the annular inflation lumen and which defines a mandrel lumen configured to receive a mandrel therein. In a presently preferred embodiment, the sidewall extends along at least a portion of an inner surface of the outer tubular member. However, the sidewall may alternatively extend along at least a portion of an outer surface of the inner tubular member. The reinforcement provided by the mandrel improves pushability and columnar strength of the catheter shaft formed from relatively soft materials, while inhibiting or preventing shaft kinking. This aids manufacturing by offering better bonding to balloon materials and allows greater flexibility in catheter design. These designs also permit a reduction in wall thickness to maximize the inflation lumen. The mandrel lumen may be configured to allow the mandrel to be exchanged to adjust the handling characteristics of the catheter. Thus, in one embodiment, the mandrel lumen extends to the proximal end of the shaft to facilitate mandrel exchange. Alternatively, the mandrel may be secured within the lumen, at one or more points on the mandrel.

Another embodiment comprises a mandrel having a proximal end distal to the proximal end of the catheter shaft. In a presently preferred embodiment, the mandrel is in an intermediate portion of the shaft between proximal and distal shaft portions. The intermediate portion typically has a length less than the length of the proximal or the distal shaft sections. The mandrel may be within a sidewall portion defining a mandrel lumen or alternatively, may be secured to the catheter shaft at the proximal and distal ends of the mandrel, or along the length thereof from the proximal to the distal end of the mandrel. In a presently preferred embodiment, the mandrel is within the lumen of a side wall which extends longitudinally along at least a portion of an inner surface of the outer tubular member. The proximal and distal portions of the outer tubular member have conventional profiles, and form the inflation lumen in conjunction with the coaxial inner tubular member. The intermediate portion has a sidewall portion configured to define a mandrel lumen along its inner surface. The mandrel is typically secured within the lumen, preferably by heat deformation. In coronary artery applications, the mandrel is configured to support the catheter as it bends through the aortic arch and enters the coronary artery. Preferably, the portion of the catheter carrying the mandrel does not enter the coronary artery.

In other embodiments, the mandrel is secured along the length of the mandrel from the proximal to the distal end thereof directly to the inner tubular member or to the outer tubular member, without a sidewall mandrel lumen. In another embodiment, the catheter has rapid exchange capabilities and generally comprises an elongated proximal tubular member having a sidewall configured to define a mandrel lumen extending longitudinally along an inner surface of the proximal tubular member. An inner tubular member overlaps the distal portion of the proximal tubular member and provides a guidewire lumen with guidewire entry and exit ports. A distal tubular member secures the adjacent portions of the proximal tubular member and the inner tubular member and carries a balloon, such as a dilatation balloon, on the distal end. The support mandrel is disposed within the mandrel lumen. Restraining the support mandrel within the lumen provides superior transmission of axial forces to improve pushability. Moreover, the dedicated lumen addresses failure concerns by allowing the catheter to be withdrawn intact in case of a mandrel fracture. When the mandrel is not confined to a dedicated lumen, a fractured end could penetrate the catheter shaft or otherwise prevent its easy removal through the tortuous vasculature.

The catheter of the invention having a mandrel has excellent crossability and trackability. The mandrel connected to the catheter shaft directly or within the dedicated mandrel lumen provides effective transmission of axial force and avoids the entanglement of the mandrel around the inner tubular member by preventing movement of the mandrel within the annular lumen. The catheter of the invention also has a low profile shaft design, and provides suitable stiffness transitions between proximal and distal portions of the catheter to improve handling and performance and minimize kinking. These and other advantages of the invention will become more apparent from the following detailed description and exemplary drawings.

BRIEF DESCRIPTION OF THE DRAWINGS

FIG. 10a is an enlarged view of an alternative embodiment of the catheter shown in FIG. 9, having a sidewall defining a mandrel lumen within a proximal section of the outer tubular member.

DETAILED DESCRIPTION OF THE INVENTION

Figure 1:
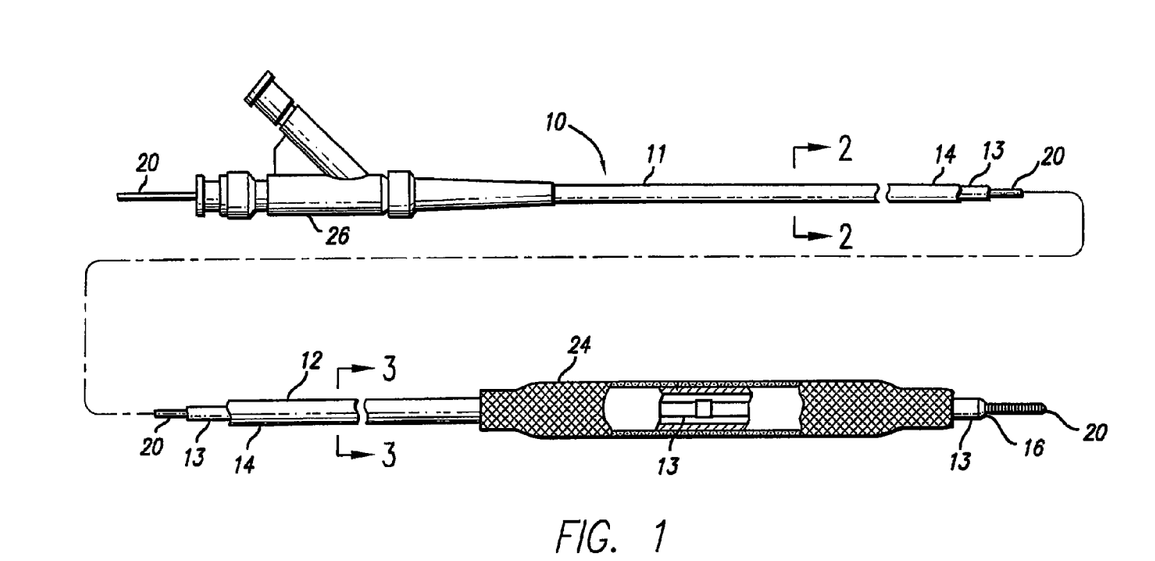
FIG. 1 is an elevational view, partially in section, of a balloon catheter which embodies features of the invention, having a dedicated mandrel lumen along an inner surface of the outer tubular member.
Figure 2:
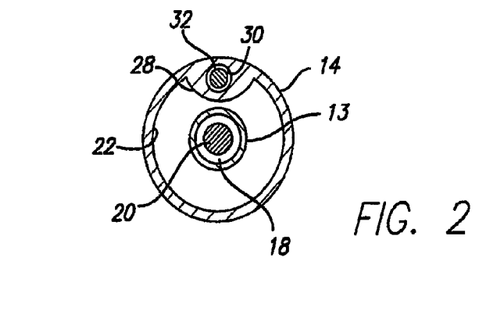
FIG. 2 is a cross sectional view of the catheter shown in FIG. 1, taken along lines 2-2.
Figure 3:
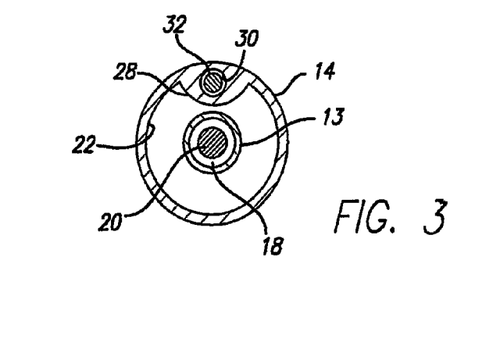
FIG. 3 is a cross sectional view of the catheter shown in FIG. 1, taken along lines 3-3.
Figure 4:
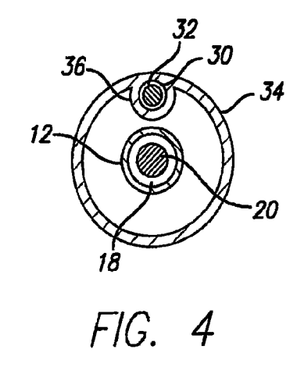
FIG. 4 is a cross sectional view of an alternate embodiment of the catheter of the invention, having a mandrel lumen defined by a sidewall secured to the outer tubular member along a transverse length of the sidewall which is less than the diameter of the side wall.

FIG. 1 illustrates a balloon catheter 10 embodying features of the invention, having a proximal shaft portion 11, a distal shaft portion 12 which is typically more flexible than proximal shaft portion 11, an inner tubular member 13, and an outer tubular member 14. Inner tubular member 13 has a guidewire port 16 at its distal end and defines a guidewire lumen 18 configured to receive guidewire 20, as best illustrated in FIGS. 2 and 3, showing transverse cross sections of the catheter shaft taken along lines 2-2 and 3-3, respectively. Outer tubular member 14 is coaxially disposed about inner tubular member 13 creating annular inflation lumen 22. A balloon 24, preferably suitable for performing an angioplasty procedure has a proximal end disposed about and secured to a distal portion of outer tubular member 14, a distal end disposed about and secured to a distal portion of the inner tubular member 13, and an interior in fluid communication with inflation lumen 22. Adapter 26 at the proximal end of catheter 10 provides fittings for access to inflation lumen 22 and guidewire lumen 18. A sidewall 28 extends longitudinally along an interior surface of outer tubular member 14, and is configured to define a mandrel lumen 30. A mandrel 32 is disposed within mandrel lumen 30.

Sidewall 28 extends from the proximal end of the catheter shaft along at least a section of the proximal shaft section 11. In a presently preferred embodiment, sidewall 28 distal end extends within the proximal shaft portion 11. However, sidewall 28 may extend within the distal shaft portion 12. In the embodiment illustrated in FIG. 1, the sidewall 28 extends within at least a section of the distal shaft portion 12. The length of the sidewall 28, and mandrel 32 therein, is about 2% to about 35% less than, and preferably about 15% to about 30% less than the length of the inner tubular member 13. The sidewall 28 and mandrel 32 are typically about 50 cm to about 140 cm long, preferably about 100 cm to about 120 cm long, for a balloon catheter of about 145 cm in length. For coronary artery applications, the mandrel 32 preferably extends through the proximal portion of the catheter so that it provides reinforcement and transmission of push through the aortic arch, but generally does not extend into the section of the catheter which extends within the coronary artery.

The diameter of mandrel 32 may be adjusted as desired to achieve the desired handling characteristics, but generally should be about 0.005 to about 0.015 inch. Preferably, the mandrel lumen 30 has an inner diameter not substantially larger than the diameter of the mandrel, i.e., about 10% to about 30%, preferably about 20% to about 25% greater than the mandrel diameter. In the embodiment illustrated in FIG. 1, the mandrel lumen is annular, although other configurations may be used depending on the shape of the mandrel. The mandrel 32 may have a tapered distal end.

Mandrel 30 may be formed from metallic materials such as stainless steel and nickel titanium alloys, as well as other pseudo-elastic or shape-memory materials, and high modulus polymers such as PEEK, PEI, Nylon, and reinforced composite rod. The inner tubular member 13 and outer tubular member 14 of the catheters of the invention may be formed by conventional techniques, e.g. extruding, from materials already found useful in intravascular catheters such a polyethylene, polyamide, polyesters and composite materials. The use of the support mandrel allows the use of otherwise soft materials, such as polyamide block copolymers, co-polyesters, nylon and polyurethanes, which are compatible with materials used to form dilatation balloons. This facilitates the bonding of the outer 14 and inner 13 tubular members to the balloon 24 by conventional techniques, such as laser bonding. The catheter components can be bonded together by heat fusion, adhesive, or by other conventional means.

In certain embodiments, adapter 26 has a third arm (not shown) providing access to mandrel lumen 30 so that mandrel 32 may be exchanged to vary the stiffness characteristics of catheter 10 to suit a given procedure. The proximal end of the mandrel 32 would extend out the proximal port in the third arm, to facilitate exchange of the mandrel. Mandrels having different flexibilities can be used and the length of the mandrel inserted into the catheter can be adjusted. For example, mandrels made from the different mandrel materials listed above, or having different diameters, may be exchanged to vary the stiffness of the catheter. In the embodiment having an exchangeable mandrel, mandrel lumen 30 is preferably sealed at the distal end of the lumen 30. Alternatively, mandrel 32 may be fixed within lumen 30, by heat deformation of sidewall 28 or with adhesive.

Figure 5:
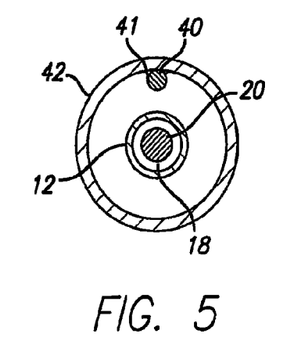
FIG. 5 is a cross sectional view of an alternate embodiment showing the support mandrel secured directly to the outer tubular member.
Figure 6:
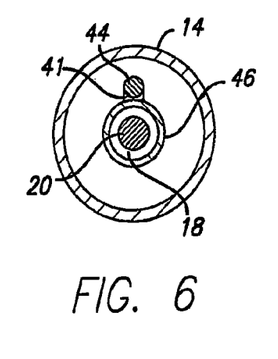
FIG. 6 is a cross sectional view of an alternate embodiment showing the support mandrel secured directly to the inner tubular member.
Figure 7:
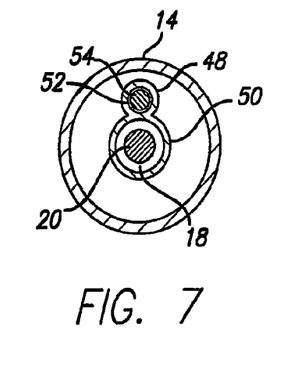
FIG. 7 is a cross sectional view of an alternate embodiment having a support mandrel lumen on an outer surface of an inner tubular member.

FIGS. 4-7 illustrate alternative embodiments for securing the mandrel 32 to the catheter shaft. In the embodiment illustrated in FIG. 4, an outer tubular member 34 has a sidewall portion 36 defining a mandrel lumen 32. The sidewall 36 is secured to the outer tubular member 14 along a transverse length of the sidewall 36. Thus, in the embodiment illustrated in FIG. 4, the side wall 36 defining the mandrel lumen 32 has an outer diameter which is less than the outer diameter of the inner tubular member. FIG. 5 illustrates another embodiment having mandrel 40 secured directly to an inner surface of outer tubular member 42, and FIG. 6 illustrates an embodiment having a mandrel 44 secured along its length to an outer surface of the inner tubular member 46. The mandrel 40/44 is secured using adhesive 41 or by heat fusing the polymer shaft to a polymeric mandrel. The mandrel 40/44 is secured along the mandrel length from the proximal end of the mandrel to the distal end of the mandrel. Alternatively, the mandrel is secured to the outer tubular member only at the proximal and the distal ends of the mandrel. FIG. 7 illustrates another embodiment having a longitudinally oriented sidewall portion 48 of inner tubular member 50 defining a mandrel lumen 52. A mandrel 54 is contained within lumen 52 and either may be fixed or exchangeable/positionable through an adapter at the proximal end of the catheter, as discussed above.

Figure 8:
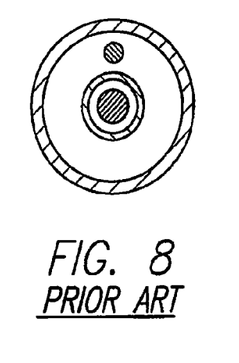
FIG. 8 is a cross sectional view of a prior art catheter having a support mandrel.

FIG. 8, illustrates a prior art over-the-wire catheter having a mandrel which is unsecured within the inflation lumen. Such prior art catheters have poor transfer of axial forces compared to the catheter of the invention. In the catheter of the invention, the mandrel has improved transfer of axial forces, thus allowing the wall thickness of the tubular members to be decreased, and consequently, the size of the inflation lumen for a given diameter catheter to be increased. The increased inflation lumen size provides for improved inflation/deflation times. The wall thickness of the inner tubular member is typically about 0.05 to about 0.2 mm, and the wall thickness of the outer tubular member is typically about 0.05 to about 0.5 mm, depending on the shaft material used.

Figure 9:
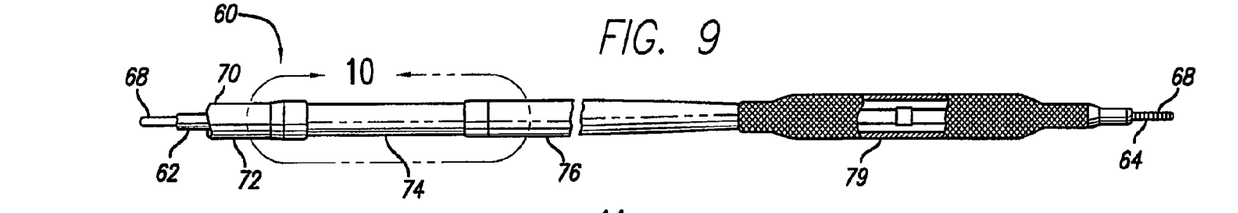
FIG. 9 is a schematic view of an embodiment of the invention which embodies features of the invention, having an intermediate support mandrel.

FIG. 9 illustrates another embodiment in which the mandrel may be confined to an intermediate section of the catheter to provide a transition between the proximal and distal portions of the catheter shaft. In the embodiment illustrated in FIG. 9, catheter 60 generally comprises inner tubular member 62 having a guidewire port 64 at the distal end and defining a lumen 66 for slidably receiving guidewire 68, and outer tubular member 70 comprising a proximal portion 72, an intermediate portion 74 and a distal portion 76. Outer tubular member 70 is coaxially disposed over inner tubular member 62 creating annular inflation lumen 78. Inflatable member 79 is in communication with inflation lumen 78.

Figure 10:
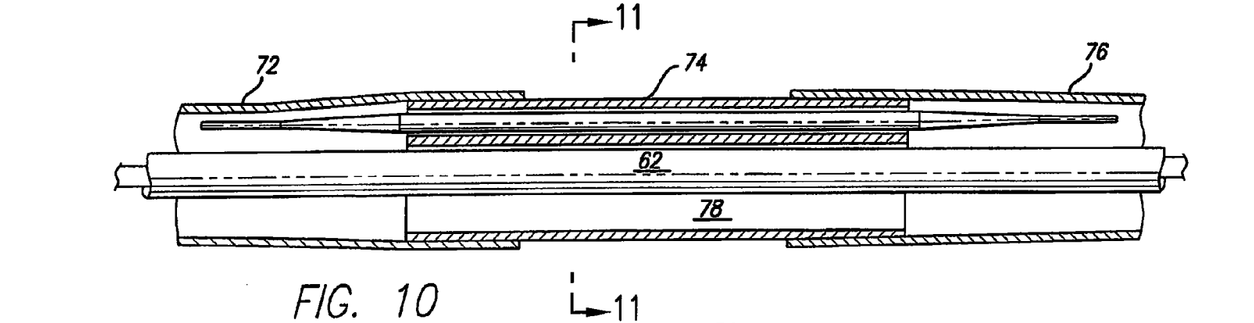
FIG. 10 is an enlarged view of the catheter shown in FIG. 9, taken within area 10.
Figure 11:
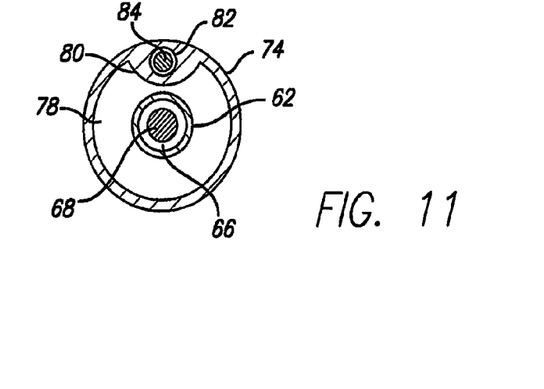
FIG. 11 is a cross sectional view taken along lines 11-11.

Intermediate portion 74 of outer tubular member 70 is shown in sectional detail in FIG. 10 and in cross section in FIG. 11. Generally, intermediate portion 74 comprises a sidewall portion 80 extending longitudinally along an inside surface, defining mandrel lumen 82. A mandrel 84 is disposed within lumen 82, providing a transition between proximal portion 72 and distal portion 76. By confining the support mandrel to an intermediate portion of the catheter shaft, less volume of annular inflation lumen 78 is used by the sidewall 80, leading to improved inflation and deflation.

The mandrel 84 is typically fixed within the lumen 82 by raising the temperature of sidewall portion 80 to cause the material to flow into the ends of the lumen 82.

In the embodiment illustrated in FIG. 9, sidewall 80 has a proximal end at the proximal end of the intermediate portion, and a distal end at the distal end of the intermediate portion. However, the sidewall 80 may have a length less than the length of the intermediate section or greater than the length of the intermediate section when the proximal portion 72 or distal portion 76 has a sidewall defining a mandrel lumen adjacent to lumen 82. The sidewall 80 and mandrel 84 therein are substantially shorter than the length of the catheter, i.e., about 5% to about 20% of the length of the catheter. The length of the sidewall 80 is typically about 5 to about 25 cm, preferably about 8 to about 20 cm. The length of the mandrel 84 is about 7 to about 27 cm, preferably about 10 to about 22 cm. The length of mandrel 84 may be varied to optimize the handling characteristics, with ends extending to or beyond the junctions between the intermediate portion 74 and the proximal portion 72 and distal portion 76. In the embodiment illustrated in FIG. 9, the mandrel 84 is ground at each end to provide a taper. This smoothes the transition between materials and minimizes the chances of an end of the mandrel puncturing the catheter. The taper extends beyond the ends of the lumen 84. In one embodiment illustrated in FIG. 10, the tapered sections of the mandrel begin beyond the ends of the lumen 84. The taper may extend to the end of the mandrel, or alternatively, a constant diameter section may be located at each end of the mandrel which extends from an end of the taper to the end of the mandrel. The mandrel may be about 0% to about 200% longer than the lumen 84, and is typically about 10% to about 30% longer than the lumen 84. The mandrel may extend from either end of the lumen 84, or from one end, as for example where mandrel extends only out the distal end of the lumen 84. For a catheter about 143 cm in overall length, the intermediate portion should be about 10 cm, while the support mandrel should be about 22 cm, with about 5 cm of taper at each end. The support mandrel may be about 0.009 inches in diameter when formed from nickel titanium. The proximal portion of the catheter is about 3.2 F while the distal portion tapers to approximately 2.4 F.

Preferably, proximal tubular portion 72, intermediate tubular portion 74 and distal tubular portion 76 are dimensioned so that the distal end of the mandrel is at, or does not extend beyond, the distal end of the guiding catheter used to introduce catheter 60 into the patient's vasculature. Thus, mandrel 84 supports catheter 60 as it bends through the aortic arch and enters the coronary artery. In such embodiments, catheter 60 may exhibit a low stiffness, high stiffness, low stiffness profile corresponding to the proximal, intermediate, and distal portions of the catheter shaft. The intermediate portion 74 is stiffened by mandrel 84, whereas the proximal 72 and distal 76 portions of catheter 60 are relatively soft since the guiding catheter can provide support for the proximal portion 72 and the distal portion 76 is formed of soft material to facilitate advancement in the coronary anatomy However, different characteristics may be obtained easily for different applications.

It may be desirable to mark the catheter shaft for fluoroscopic visualization. However, the sidewall 30/80 does not allow uniform support of the tubular member, complicating the use of conventional marking techniques. By limiting the sidewall 80 of outer tubular member to the intermediate portion 74, the proximal portion 72 of outer tubular member 70 may be marked in a conventional manner. Additionally, the configuration provides for improved inflation/deflation times.

As discussed above, the inner and outer tubular members may be formed from materials already found suitable for catheter manufacture. In one preferred embodiment, proximal, intermediate, and distal portions of the outer tubular member are formed of different materials providing a flexibility increasing from the proximal to the distal end of the catheter. In a presently preferred embodiment, proximal portion 72, is formed from a Nylon blend, the intermediate portion 74 is formed from a Nylon, and the distal portion 76 is formed from a polyamide copolymer such as PEBAX. The inner tubular ember may have proximal, intermediate and distal portions similar to the outer tubular member.

In an alternative embodiment (not shown), intermediate portion 74 does not have sidewall 80, and the mandrel 84 is secured directly to the outer tubular member 70 or the inner tubular member 62 at the intermediate portion 74. Preferably, the mandrel 84 is bonded to the tubular member 70/62 with adhesive, although other conventional means of attachment may also be used. The mandrel 84 can be attached at two points adjacent its ends, at intermediate points or along its entire length. The adhered support mandrel is preferably used with catheter shafts having different materials for the proximal and distal outer tubular member portions, to ease the transition between the two materials.

In the embodiment illustrated in FIG. 9, intermediate portion 74 is a separate section joined to the proximal and distal ends of the distal 76 and proximal 72 portions, respectively. The intermediate portion 74 extends within the proximal 72 and distal 76 portions, although other suitable joints may be used to join the shaft portions together. Alternatively, the intermediate portion 74 can be eliminated and the mandrel 84 may be confined to a location within the proximal end of the distal portion 76, or the distal end of the proximal portion 72, or it may extend from the proximal portion 72 to the distal portion 76

Figures 12, 13:
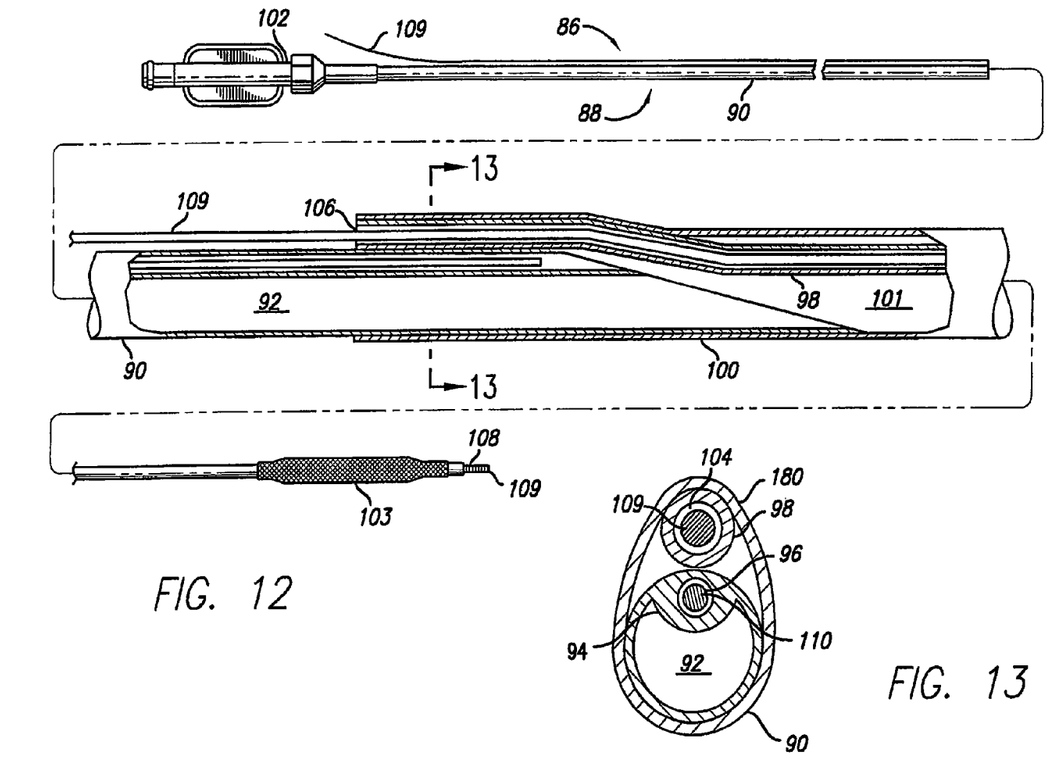
FIG. 12 is a schematic view of a catheter of the invention which embodies features of the invention, having rapid exchange capabilities.
FIG. 13 is a cross sectional view of the catheter shown in FIG. 12 taken along lines 13-13.

In yet another embodiment of the invention, shown in FIGS. 12 and 13, catheter 86 is configured to have rapid exchange capabilities. Generally catheter shaft 88 comprises an elongated proximal tubular member 90 which defines inflation lumen 92. Along an inner surface of proximal tubular member 90 is a longitudinally oriented sidewall portion 94 that defines support mandrel lumen 96. A proximal portion of inner tubular member 98 is adjacent to a distal portion of proximal tubular member. Distal tubular member 100 is coaxially disposed about proximal tubular member 90 and inner tubular member 98. Accordingly, the proximal end of distal tubular member 100 overlaps and seals the proximal portion of inner tubular member 98 and the distal portion of proximal tubular member 90 as shown in cross section in FIG. 13. Distal tubular member defines a lumen 101 that is in communication with inflation lumen 92. Adapter 102 at the proximal end of catheter shaft 88 provides access to inflation lumen 92. An inflatable member 103 at the distal end of the catheter is likewise in communication with lumen 101. Inner tubular member 98 defines guidewire lumen 104 and has a first guidewire port 106 at its proximal end and a second guidewire port 108 at its distal end configured to receive guidewire 109. Support mandrel 110 is disposed within support mandrel lumen 96 and preferably is secured within the lumen but may also be exchangeable.

Suitable materials, such as those already discussed, may be used to fabricate the tubular members of the catheter shaft 88. Generally the support mandrel 110 is configured to give a level of reinforcement equivalent to convention rapid exchange catheters having a proximal hypotube. Presently preferred materials include stainless steel and nickel titanium alloys, with MP35N and 304 stainless steel particularly preferred. Mandrel 110 should have a length about equal to the proximal portion of the catheter, such as approximately 115 cm for a typical PTCA procedure. If desired, the distal portion of mandrel 110 can be radiused or tapered to maximize flexibility without causing kinking at the transition. Distal end of mandrel 110 can be about 20 to 25 cm from the distal end of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A catheter for performing an intravascular procedure, comprising
   a) a catheter shaft comprising an inner and outer tubular member fixedly secured together, and the inner tubular member defines a first lumen located within the inner tubular member, and the inner tubular member has an outer diameter that is smaller than an outer diameter of the outer tubular member, and the inner tubular member is disposed within the outer tubular member such that a second ring-shaped lumen extends between an inner surface of the outer tubular member and an outer surface of the inner tubular member;
   b) a side wall which extends longitudinally along the outer surface of at least a portion of the inner tubular member within the second lumen and which defines a third lumen configured to receive a mandrel, and which is radially spaced apart from the inner surface of the outer tubular member by the second lumen extending fully around an inner circumference of the outer tubular member, the side wall having an outer diameter measured through a center of the third lumen that is smaller than an outer diameter of the inner tubular member measured through a center of the first lumen; and
   c) a mandrel in the third lumen.

2. The catheter claim 1, wherein the mandrel has tapered ends.

3. The catheter of claim 2, wherein the tapered ends of the mandrel are about 1 to about 7 centimeters long.

4. The catheter of claim 1, wherein the mandrel is about 7 to about 120 centimeters long.

5. The catheter of claim 1, wherein the mandrel is secured within the mandrel lumen by heat deformation of the sidewall.

6. The catheter of claim 1, wherein the mandrel lumen has an inner diameter which is not substantially larger than an outer diameter of the mandrel.

7. The catheter of claim 1, wherein the mandrel lumen proximal end is distal to the proximal end of the catheter inner tubular member.

8. The catheter of claim 7, wherein the mandrel lumen is about 0.5 to about 15 centimeters long.

9. The catheter of claim 7 wherein the inner tubular member has a proximal portion, a distal portion, and an intermediate portion therebetween, and wherein the mandrel lumen is within the intermediate portion.

10. The catheter of claim 9, wherein the intermediate portion with the mandrel within the mandrel lumen therein is relatively more stiff than the proximal portion and the distal portion.

11. The catheter of claim 1 wherein the mandrel lumen extends to the proximal end of the inner tubular member.

12. The catheter of claim 11 wherein the mandrel lumen is about 110 to about 125 cm long.

13. The catheter of claim 11, wherein the mandrel is exchangeable.

14. The catheter of claim 1 wherein the mandrel has a length substantially shorter than a length of the catheter.

15. The catheter of claim 1 wherein the third lumen has a length substantially shorter than a length of the cathete.

* * * * *

UNITED STATES PATENT AND TRADEMARK OFFICE
CERTIFICATE OF CORRECTION

| | | |
|---|---|---|
| PATENT NO. | : 7,351,238 B2 | Page 1 of 1 |
| APPLICATION NO. | : 10/692365 | |
| DATED | : April 1, 2008 | |
| INVENTOR(S) | : Jeong Soo Lee et al. | |

It is certified that error appears in the above-identified patent and that said Letters Patent is hereby corrected as shown below:

Column 3, delete lines 39 through 42.

Column 6, line 60, delete "anatomy However" and insert --anatomy. However--.

Column 7, line 14, delete "ember" and insert --member--.

Column 8, line 1, delete "convention" and insert --conventional--.

Signed and Sealed this

Twelfth Day of August, 2008

JON W. DUDAS
*Director of the United States Patent and Trademark Office*